United States Patent [19]

Carson

[11] 4,213,905
[45] Jul. 22, 1980

[54] PREPARATION OF 5-AROYL-1-LOWERALKYLPYRROLE-2-ACETIC ACID SALTS

[75] Inventor: John R. Carson, Norristown, Pa.

[73] Assignee: McNeilab, Inc., Fort Washington, Pa.

[21] Appl. No.: 51,646

[22] Filed: Jun. 25, 1979

[51] Int. Cl.$^2$ ............................................. C07D 207/32
[52] U.S. Cl. ........................... 260/326.47; 260/326.5 J
[58] Field of Search .................................... 260/326.47

[56] References Cited

U.S. PATENT DOCUMENTS

| | | | |
|---|---|---|---|
| 3,721,680 | 3/1973 | Carson | 260/326.47 |
| 3,752,826 | 8/1973 | Carson | 260/326.5 J |
| 3,808,171 | 4/1974 | Carson | 260/326.47 |
| 3,998,844 | 12/1976 | Carson | 260/326.47 |
| 4,048,191 | 9/1977 | Carson | 260/326.47 |
| 4,070,368 | 1/1978 | Carson | 260/326.47 |

Primary Examiner—Mary C. Lee

[57] ABSTRACT

5-Aroyl-1-loweralkylpyrrole-2-acetonitriles are converted to the corresponding thiol esters by treatment with an alkyl mercaptan under acidic conditions followed by basification of the thiol esters to the corresponding acid salt form.

15 Claims, No Drawings

PREPARATION OF 5-AROYL-1-LOWERALKYLPYRROLE-2-ACETIC ACID SALTS

BACKGROUND OF THE INVENTION

5-Aroyl-1-loweralkylpyrrole-2-acetic acids and salts thereof have been described in the literature as potent anti-inflammatory agents (see, for example, U.S. Pat. No. 3,752,826).

The nitrile-to-acid salt conversion described by the present invention has the advantage of faster reaction times over the prior art alkaline hydrolysis method. For example, the convesion of 5-(p-toluoyl)-1-methylpyrrole-2-acetonitrile to the corresponding acid salt form according to Examples III and IV hereinafter may be accomplished in about 5½ hours as compared to about 18 hours for complete NaOH hydrolysis of the nitrile.

DESCRIPTION OF THE INVENTION

This invention relates to an improved process of preparing alkali metal and alkaline earth metal salts of 5-aroyl-1-loweralkylpyrrole-2-acetic acids having the formula:

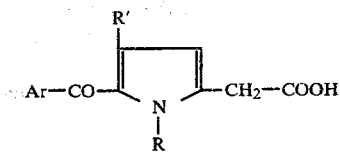

wherein
R is loweralkyl, preferably methyl;
R' is a member selected from the group consisting of hydrogen and loweralkyl, preferably methyl; and
Ar is a member selected from the group consisting of phenyl and phenyl substituted with from one to three substituents each selected from the group consisting of loweralkyl, loweralkoxy and halo.

As used herein, the prefix "lower" is meant to represent straight or branch chained saturated hydrocarbons having from 1 to about 5 carbon atoms, such as, for example, methyl, ethyl, propyl, isopropyl, butyl, pentyl and the like alkyls, and the corresponding alkoxys such as methoxy, ethoxy, propoxy, isopropoxy, etc. The term "halo" is generic to chloro, bromo, fluoro and iodo. Among the preferred substituted phenyls are those wherein "Ar" is loweralkylphenyl and halophenyl, the most preferred being p-methylphenyl and p-chlorophenyl.

In accordance with this invention, there is provided an improved process of synthesizing a 5-aroyl-1-loweralkylpyrrole-2-acetic acid and salts thereof by reacting a 5-aroyl-1-loweralkylpyrrole-2-acetonitrile with an alkyl mercaptan in the presence of a mineral acid in an anhydrous aprotic solvent under an inert atmosphere and then hydrolyzing the thus-obtained thiol ester by treatment with a loweralkanolic solution of an alkali metal or alkaline earth metal hydroxide to yield the corresponding metallic acid salt which is then acidified to yield the corresponding 5-aroyl-1-loweralkylpyrrole-2-acetic acid.

According to the subject invention, a 5-aroyl-1-loweralkylpyrrole-2-acetonitrile (described in U.S. Pat. No. 3,752,826) of formula (II) is reacted with an alkyl mercaptan of formula (III) in the presence of a mineral acid under anhydrous conditions to form the corresponding thiol ester of formula (IV). The reaction is conducted in an aprotic organic solvent under an inert atmosphere such as nitrogen, argon and the like at temperatures at or below 10° C. and preferably from about −40° C. to about 10° C. Typical mercaptans (III) that may preferably be employed are methyl, ethyl, butyl, and the like loweralkyl mercaptans although higher alkyl mercaptans may also be suitable. Among the suitable aprotic solvents are aromatic hydrocarbons such as, for example, benzene, toluene, xylene, p-cymene and the like; substituted aromatic hydrocarbons such as, for example, chlorobenzene, dichlorobenzene, nitrobenzene and the like; halocarbons such as, for example, methylene chloride, chloroform, tetrachloroethane and the like; ethers such as, for example, diethyl ether, diglyme, dioxane, tetrahydrofuran and the like; and such other inert organic liquids capable of acting as a solvent for the reactants without interfering with the reaction itself. Suitable mineral acids include hydrochloric, hydrobromic and sulfuric acid. Preferably, hydrogen chloride or hydrogen bromide gas is bubbled through the reaction medium.

The thus-obtained thiol ester (IV) is then hydrolyzed by treatment with an aqueous solution of base such as an alkali metal or alkaline earth metal hydroxide, for example, sodium or potassium hydroxide, barium hydroxide and the like according to alkaline hydrolysis methodologies to yield the corresponding metallic acid salt such as, for example, the sodium salt shown in formula (V). Although not essential, a small amount of a lower alkanol such as methanol, ethanol and the like is preferably added. Elevated temperatures may be employed to enhance the rate of reaction.

Conventional acidification of (V), for example, with hydrohalic, sulfuric, phosphoric, nitric and the like acids, yields the corresponding acid products of formula (I).

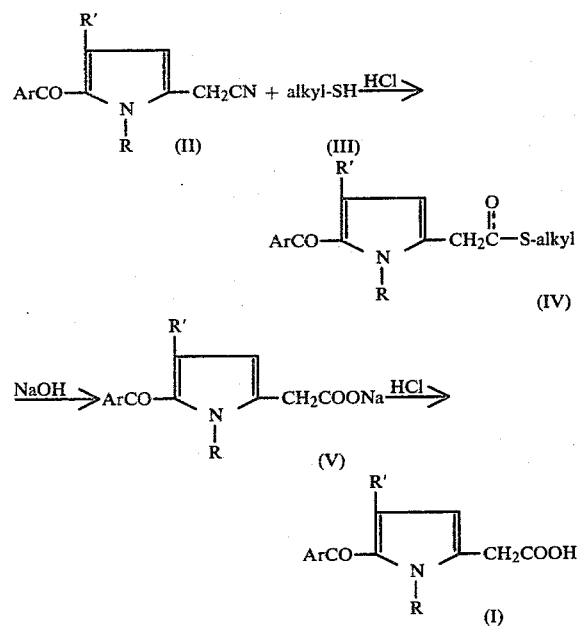

The hereinabove described step of converting nitrile (II) to thiol ester (IV) is deemed novel and, accordingly, such conversion constitutes an additional feature of this invention.

The following examples are intended to illustrate, but not to limit, the scope of the present invention. Unless otherwise stated, all parts are by weight.

EXAMPLE I

Ethyl 5-(p-Chorobenzoyl)-1,4-dimethylpyrrole-2-thiolacetate:

To a dry 100 ml 3-necked round-bottom flask under nitrogen is added 5-(p-chlorobenzoyl)-1,4-dimethylpyrrole-2-acetonitrile (1.4 g. 0.0051 mole) and 25 ml of dry tetrahydrofuran (THF). The solution is cooled to −25° C., ethyl mercaptan (0.39 ml, 0.0051 mole) is added, and hydrogen chloride is bubbled into the reaction mixture. After 1.5 hrs the reaction mixture is saturated with HCl and the temperature is raised to and maintained at 0° C. for three hrs. The reaction mixture is then poured into toluene and steam is bubbled into the toluene mixture. The toluene layer is then separated, washed with brine and dried over anhydrous $MgSO_4$. The toluene solvent is rotoevaporated to give 1.7 g of crude product which is recrystallized twice from methanol to yield 0.57 g (33.5%) of pure ethyl 5-(p-chlorobenzoyl)-1,4-dimethylpyrrole-2-thiolacetate; m.p. 90.5°–92° C.

EXAMPLE II

Sodium 5-(p-chlorobenzoyl)-1,4-dimethylpyrrole-2-acetic acid

To a 25 ml round-bottom flask is added ethyl 5-(p-chlorobenzoyl)-1,4-dimethylpyrrole-2-thiolacetate (0.40 g), 5 ml IN NaOH and four drops of 95% ethanol. The solution is refluxed for one hour and then cooled in an ice-bath. 7 Ml of 25% NaOH is added and the resultant sodium salt product is filtered and recrystallized once from 95% ethanol to yield 0.25 g of sodium 5-(p-chlorobenzoyl)-1,4-dimethylpyrrole-2-acetate, m.p. 307°–9° C. Acidification with dilute HCl yields the free acid, 5-(p-chlorobenzoyl)-1,4-dimethylpyrrole-2-acetic acid.

EXAMPLE III

Ethyl 1-methyl-5-(p-toluoyl)pyrrole-2-thiolacetate

To a dry 100 ml three-necked flask under nitrogen is added 1-methyl-5-(p-toluoyl)pyrrole-2-acetonitrile (4.0 g, 0.0168 mole) and 30 ml of dry THF. The solution is cooled to −20° C., ethyl mercaptan (1.38 ml, 0.0180 mole) is added and hydrogen chloride is then bubbled into the reaction mixture. When the reaction mixture is saturated with HCl the temperature is raised to and maintained at 0° C. for 2.5 hrs. The reaction mixture is poured into a three-necked, 300 ml round-bottom flask, 100 ml of toluene is added and steam blown into the organic layer until the red color disappears. The toluene layer is separated and the water layer washed twice with toluene. The toluene extracts are combined, washed with brine and dried over anhydrous $MgSO_4$. The solvent is evaporated in vacuo to yield 4.27 g (84.4%) of crude product. One recrystallization from methanol yields 2.15 g (42.5%) of ethyl 1-methyl-5-(p-toluoyl)-pyrrole-2-thiolacetate, m.p. 74°–76° C.

EXAMPLE IV

Sodium-1-methyl-5-(p-toluoyl)pyrrole-2-acetic acid

To a round-bottom flask is added ethyl 5-(p-toluoyl)-1-methylpyrrole-2-thiolacetate (0.55 g), 0.5 N NaOH (7.3 ml) and four drops of 95% ethanol. The solution is refluxed for 1.5 hrs. One ml of 25% NaOH is then added and reflux continued for an additional two hours. The solution is cooled, 3 ml of 25% NaOH is added and the sodium salt product filtered (0.49 g; 96.1%) and recrystallized once from ethanol to yield 0.30 g of sodium 1-methyl-5-(p-toluoyl)-pyrrole-2-acetate. (Note: I.R. analysis, nujol mull, and m.p. of this material are identical to those of known tolmetin sodium). Acidification of the sodium salt with dilute HCl yields 1-methyl-5-(p-toluoyl)pyrrole-2-acetic acid.

EXAMPLE V

The procedure of Example (I) is repeated except that an equivalent amount of each of the following acetonitriles is substituted for the 5-(p-chlorobenzoyl)-1,4-dimethylpyrrole-2-acetonitrile used therein as the starting material to be treated with ethyl mercaptan:

5-(p-ethoxybenzoyl)-1-ethylpyrrole-2-acetonitrile;
5-(p-chlorobenzoyl)-1-methylpyrrole-2-acetonitrile;
5-(p-bromobenzoyl)-1-methylpyrrole-2-acetonitrile;
5-(2,4,6-trimethylbenzoyl)-1-ethylpyrrole-2-acetonitrile;
5-(2,4-dichlorobenzoyl)-1-butylpyrrole-2-acetonitrile;
5-(2,4-dimethoxybenzoyl)-1-methylpyrrole-2-acetonitrile;
5-(p-ethoxybenzoyl)-1,4-dimethylpyrrole-2-acetonitrile;
5-(p-toluoylbenzoyl)-1,4-dimethylpyrrole-2-acetonitrile; and
5-(p-2,4,6-trichlorobenzoyl)-1,4-dimethylpyrrole-2-acetonitrile, to yield as respective end products the corresponding ethyl thiolacetates.

EXAMPLE VI

By substituting an equivalent amount of each ethyl thiolacetate obtained in Example V as the starting material to be hydrolyzed according to the procedure of Example II, the following acid products are respectively obtained:

5-(p-ethoxybenzoyl)-1-ethylpyrrole-2-acetic acid;
5-(p-chlorobenzoyl)-1-methylpyrrole-2-acetic acid;
5-(p-bromobenzoyl)-1-methylpyrrole-2-acetic acid;
5-(2,4,6-trimethylbenzoyl)-1-ethylpyrrole-2-acetic acid;
5-(2,4-dichlorobenzoyl)-1-butylpyrrole-2-acetic acid;
5-(2,4-dimethoxybenzoyl)-1-methylpyrrole-2-acetic acid;
5-(p-ethoxybenzoyl)-1,4-diomethylpyrrole-2-acetic acid;
5-(p-toluoylbenzoyl)-1,4-dimethylpyrrole-2-acetic acid; and
5-(p-2,4,6-trichlorobenzoyl)-1,4-dimethylpyrrole-2-acetic acid.

EXAMPLE VII

Barium 5-(p-chlorobenzoyl)-1,4-dimethylpyrrole-2-acetate

The procedure of Example I is repeated except that an equivalent quantity of methyl mercaptan is substituted for the ethyl mercaptan employed therein to yield, as the respective thiol ester, methyl 5-(p-chlorobenzoyl)-1,4-dimethylpyrrole-2-thiolacetate. Alkaline hydrolysis of said thiol ester according to the procedure of Example II, using an equivalent amount of barium hydroxide in lieu of sodium hydroxide, yields the corresponding barium salt, barium 5-(p-chlorobenzoyl)-1,4-dimethylpyrrole-2-acetate.

EXAMPLE VIII

Potassium 1-methyl-5-(p-toluoyl)pyrrole-2-acetic acid

By repeating the procedure of Example III, except that an equivalent quantity of butyl mercaptan is substituted for the ethyl mercaptan used therein, the respective thiol ester, butyl 1-methyl-5-(p-toluoyl)pyrrole-2-thiolacetate, is obtained. Alkaline hydrolysis of said thiol ester according to the procedure of Example IV, except that an equivalent amount of potassium hydroxide is substituted for the sodium hydroxide, yields the corresponding potassium salt, potassium 1-methyl-5-(p-toluoyl)pyrrole-2-acetic acid.

I claim:

1. A process of preparing an alkali metal or alkaline earth metal salt of 5-aroyl-1-loweralkylpyrrole-2- acetic acid having the formula:

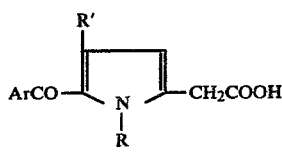

which comprises reacting a 5-aroyl-1-loweralkylpyrrole-2-acetonitrile having the formula:

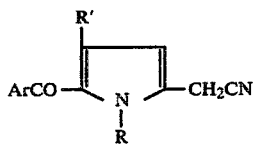

with an alkyl mercaptan in the presence of mineral acid in an anhydrous aprotic organic solvent under an inert atmosphere at or below 10° C. to yield a thiol ester having the formula:

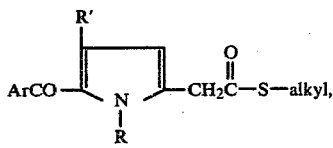

and then hydrolyzing said thiol ester by treatment with an aqueous solution of an alkali metal or alkaline earth metal hydroxide, wherein the above formulas, R is loweralkyl, R' is a member selected from the group consisting of hydrogen and loweralkyl, and Ar is a member selected from the group consisting of phenyl and phenyl substituted with from one to three substituents each selected from the group consisting of loweralkyl, loweralkoxy and halo.

2. The process of claim 1 wherein said alkyl mercaptan is ethyl mercaptan and said mineral acid is hydrogen chloride.

3. The process of claim 1 wherein said alkali metal hydroxide is sodium hydroxide.

4. The process of claim 1 wherein said R is methyl and said R' is hydrogen.

5. The process of claim 1 wherein each of said R and R' is methyl.

6. A process of preparing an alkali metal or alkaline earth metal salt of 5-aroyl-1-methylpyrrole-2-acetic acid having the formula:

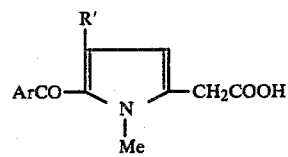

which comprises reacting a 5-aroyl-1-methylpyrrole-2-acetonitrile having the formula:

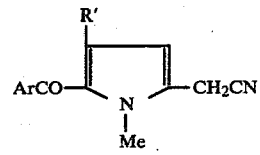

with a loweralkyl mercaptan in the presence of mineral acid in an anhydrous aprotic organic solvent under an inert atmosphere at or below 10° C. to yield a thiol ester having the formula:

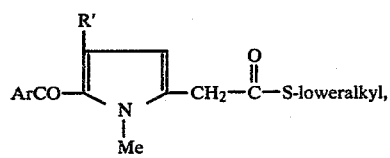

and then hydrolyzing said thiol ester by treatment with an aqueous solution of an alkali metal or alkaline earth metal hydroxide, wherein the above formulas, R' is a member selected from the group consisting of hydrogen and loweralkyl, and Ar is a member selected from the group consisting of phenyl and phenyl substituted with from one to three substituents each selected from the group consisting of loweralkyl, loweralkoxy and halo.

7. A process of preparing sodium 5-(p-chlorobenzoyl)-1,4-dimethylpyrrole-2-acetic acid which comprises reacting 5-(p-chlorobenzoyl)-1,4-dimethylpyrrole-2-acetonitrile with ethyl mercaptan in the presence of hydrogen chloride in an anhydrous aprotic organic solvent under an inert atmosphere at or below 10° C. to yield ethyl 5-(p-chlorobenozyl)- 1,4-dimethylpyrrole-2-thiolacetate and then hydrolyzing said thiolacetate by treatment with aqueous sodium hydroxide.

8. A process of preparing sodium 1-methyl-5-(p-toluoyl)- pyrrole-2-acetic acid which comprises reacting 1-methyl-5- (p-toluoyl)pyrrole-2-acetonitrile with ethyl mercaptan in the presence of hydrogen chloride in an anhydrous aprotic organic solvent under an inert atmosphere at or below 10° C. to yield ethyl 1-methyl-5-(p-toluoyl)pyrrole-2-thiolacetate and then hydrolyzing said thiolacetate by treatment with aqueous sodium hydroxide.

9. A process of preparing a thiol ester having the formula:

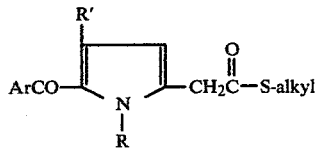

which comprises reacting a 5-aroyl-1-loweralkylpyrrole- 2-acetonitrile having the formula:

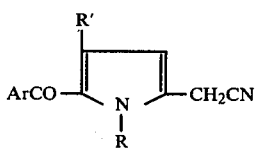

with an alkyl mercaptan in the presence of mineral acid is an anhydrous aprotic organic solvent under an inert atmosphere at or below 10° C., where in the above formulas R is loweralkyl, R' is a member selected from the group consisting of hydrogen and loweralkyl, and Ar is a member selected from the group consisting of phenyl and phenyl substituted with from one to three substituents each selected from the group consisting of loweralkyl, loweralkoxy and halo.

10. The process of claim 9 wherein said alkyl mercaptan is ethyl mercaptan and said mineral acid is hydrogen chloride.

11. The process of claim 9 wherein said R is methyl and said R' is hydrogen.

12. The process of claim 9 wherein each of said R and R' is methyl.

13. A process of preparing a thiol ester having the formula:

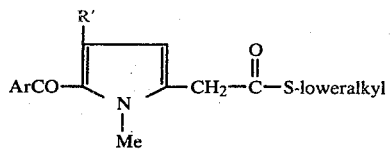

which comprises reacting a 5-aroyl-1-methylpyrrole-2-acetonitrile having the formula:

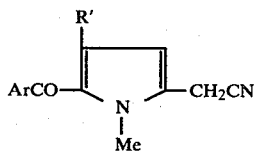

with a loweralkyl mercaptan in the presence of mineral acid in an anhydrous aprotic organic solvent under an inert atmosphere at or below 10° C. wherein the above formulas R' is a member selected from the group consisting of hydrogen and loweralkyl, and Ar is a member selected from the group consisting of phenyl and phenyl substituted with from one to three substituents each selected from the group consisting of loweralkyl, loweralkoxy and halo.

14. A process of preparing ethyl 5-(p-chlorobenzoyl)-1, 4-dimethylpyrrole-2-thiolacetate which comprises reacting 5-(p-chlorobenzoyl)-1,4-dimethylpyrrole-2-acetonitrile with ethyl mercaptan in the presence of hydrogen chloride in an anhydrous aprotic solvent under an inert atmosphere at or below 10° C.

15. A process of preparing ethyl 1-methyl-5-(p-toluoyl)- pyrrole-2-thiolacetate which comprises reacting 1-methyl- 5-(p-toluoyl)pyrrole-2-acetonitrile with ethyl mercaptan in the presence of hydrogen chloride in an anhydrous aprotic solvent under an inert atmosphere at or below 10° C.

* * * * *